United States Patent
Grady et al.

(10) Patent No.: US 10,607,739 B2
(45) Date of Patent: *Mar. 31, 2020

(54) SYSTEMS AND METHODS FOR ANATOMICAL MODELING USING INFORMATION OBTAINED FROM A MEDICAL PROCEDURE

(71) Applicant: HeartFlow, Inc., Redwood City, CA (US)

(72) Inventors: Leo Grady, Millbrae, CA (US); Charles A. Taylor, Menlo Park, CA (US); Campbell Rogers, Portola Valley, CA (US); Christopher K. Zarins, Menlo Park, CA (US); Gilwoo Choi, Mountain View, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/260,740

(22) Filed: Jan. 29, 2019

(65) Prior Publication Data

US 2019/0156957 A1    May 23, 2019

Related U.S. Application Data

(63) Continuation of application No. 15/347,592, filed on Nov. 9, 2016, now Pat. No. 10,236,084.

(60) Provisional application No. 62/253,566, filed on Nov. 10, 2015.

(51) Int. Cl.
*G16H 50/50*  (2018.01)

(52) U.S. Cl.
CPC ................... *G16H 50/50* (2018.01)

(58) Field of Classification Search
CPC ................. G16H 50/50; G06F 19/3437
See application file for complete search history.

(56) References Cited

U.S. PATENT DOCUMENTS

| | | | |
|---|---|---|---|
| 9,058,692 B1 | 6/2015 | Grady et al. | |
| 10,236,084 B2 * | 3/2019 | Grady | G16H 50/50 |
| 2010/0266172 A1 | 10/2010 | Shlomi | |
| 2012/0084064 A1 | 4/2012 | Dzenis et al. | |
| 2014/0022250 A1 | 1/2014 | Mansi et al. | |
| 2015/0199478 A1 | 7/2015 | Bhatia et al. | |

OTHER PUBLICATIONS

International Search Report for corresponding Application No. PCT/US2016/061155, dated Feb. 6, 2017 (5 pages).

* cited by examiner

*Primary Examiner* — Nicholas J Tobergte
(74) *Attorney, Agent, or Firm* — Bookoff McAndrews, PLLC (57) ABSTRACT

Systems and methods are disclosed herein for anatomical modeling using information obtained during a medical procedure, whereby an initial anatomical model is generated or obtained, a correspondence is determined between the initial model and additional data and/or measurements from an invasive or noninvasive procedure, and, if a discrepancy is found between the initial model and the additional data, the anatomical model is updated to incorporate the additional data and reduce the discrepancy.

17 Claims, 5 Drawing Sheets

SYSTEMS AND METHODS FOR ANATOMICAL MODELING USING INFORMATION OBTAINED FROM A MEDICAL PROCEDURE

PRIORITY

This application is a continuation of and claims the benefit of priority to U.S. application Ser. No. 15/347,592, filed on Nov. 9, 2016, which claims the benefit of priority from U.S. Provisional Application No. 62/253,566, filed on Nov. 10, 2015, which are incorporated by reference herein in their entireties.

TECHNICAL FIELD

Various embodiments of the present disclosure relate generally to medical imaging and related methods. More specifically, particular embodiments of the present disclosure relate to systems and methods for anatomical modeling using information obtained from a medical procedure.

BACKGROUND

Heart disease, such as coronary artery disease, may produce coronary lesions such as a stenosis (abnormal narrowing of a blood vessel) in the blood vessels that provide blood to and/or from the heart. As a result, blood flow to the heart may be restricted. A patient suffering from coronary artery disease may experience chest pain, referred to as chronic stable angina (during physical exertion) or unstable angina (when the patient is at rest). A more severe manifestation of disease may lead to myocardial infarction, or heart attack.

Anatomical modeling by noninvasive imaging may benefit a patient by assisting a physician in determining the severity of a disease and a possible treatment or treatments. Such noninvasive imaging and anatomical modeling may be performed using, for example, the systems and methods described in U.S. Pat. No. 8,315,812, filed on Jan. 25, 2011 by Charles A. Taylor, which is incorporated by reference herein in its entirety. Such anatomical modeling may be accompanied by, for example, automated identification of treatment options from a plurality of feasible treatment options (e.g., all possible percutaneous coronary intervention (PCI) or coronary artery bypass grafting (CABG) options), by analyzing noninvasively assessed coronary anatomy, and automatically designing, defining, or otherwise identifying a customized or personalized cardiac implant or other intervention for a specific patient, by analyzing noninvasively assessed coronary anatomy. For example, a recommended treatment option may be generated by an automated system, such as one or more of those described in, for example, U.S. Pat. No. 9,449,146, filed on Jul. 3, 2014 by Ryan Spilker et al., or U.S. Pat. No. 9,043,190, filed on Apr. 16, 2014 by Leo Grady et al, both of which are incorporated by reference herein in their entireties.

In addition to being subjected to noninvasive imaging that may be used to model and assess their coronary anatomy, patients suffering from chest pain and/or exhibiting symptoms of coronary artery disease may be subjected to one or more invasive or noninvasive procedures that may provide supplemental, more accurate, and/or more current data relating to coronary lesions and/or the anatomy of the heart. Such procedures may include, for example, electrocardiograms, biomarker evaluation from blood tests, treadmill tests, echocardiography, single positron emission computed tomography (SPECT), positron emission tomography (PET), and coronary computed tomographic angiography (CCTA). Moreover, if a patient has been determined to require interventional treatment, additional measurements may be taken via invasive or noninvasive methods during an interventional procedure (e.g., via angiogram, pressure wire, optical coherence tomography (OCT), intravascular ultrasound (IVUS), flow meters, intravascular optical imaging, external cameras in the interventional suite or operating room, etc.).

Cardiologists and other health care professionals may analyze images, models and/or other data obtained prior to an interventional and/or diagnostic procedure, when determining if and whether a suitable intervention for improving a patient's cardiovascular blood flow is necessary. However, when such data are obtained prior to an interventional and/or diagnostic procedure, their accuracy and/or precision may vary, e.g., over time as a patient's system changes or ages. Data obtained during an interventional and/or diagnostic procedure, in contrast, may be more accurate and/or more current, but may not provide a holistic view of the patient's system. Moreover, cardiologists and other medical professionals may not be able to conduct an analysis and interpretation of such data in order to make an assessment of, and make decisions for further interventional measures based on, such data, while simultaneously performing a diagnostic and/or interventional procedure.

A need exists for anatomical modeling using information obtained during a medical procedure. In addition, a need exists for a system and method for providing an updated anatomical model, one or more modeled interventional procedures, one or more recommended procedures based on the updated anatomical model, and/or one or more modeled interventional procedures to a physician or other medical professional during a medical procedure, using information obtained during the medical procedure.

SUMMARY

In some embodiments of the present disclosure, systems and methods are disclosed for anatomical modeling using information obtained during a medical procedure. In some embodiments, a method of automatically updating a cardiovascular model includes receiving an anatomical model of at least one cardiovascular vessel; receiving at least one characteristic associated with the anatomical model, transmitting a representation of at least one of the anatomical model or the at least one associated characteristic to a display unit, receiving additional patient-specific data relating to the anatomical model from a medical procedure, determining a correspondence between the additional patient-specific data and at least one of the anatomical model or the at least one associated characteristic, identifying a discrepancy between the additional patient-specific data and at least one of the anatomical model or the at least one associated characteristic, modifying at least one of the anatomical model or the at least one associated characteristic to reduce the discrepancy, and transmitting an updated representation of at least one of the anatomical model or the at least one associated characteristic to the display unit.

In some embodiments, the method includes modeling an intervention or a part thereof on the anatomical model and transmitting a representation of the modeled intervention or part thereof to the display unit. In some embodiments, the method includes generating at least one recommendation of an intervention on the patient based on at least one of the three-dimensional anatomical model or the at least one associated characteristic, and transmitting the at least one recommendation to the display unit. In some embodiments, the intervention is one or more of: insertion of an endoscopic device, a laparoscopic device, a stent, a prosthetic implant, a graft, or a needle; a bypass grafting procedure; a rotablation; an atherectomy; an angioplasty; an endarterectomy; a percutaneous coronary intervention; a carotid intervention; a peripheral intervention; a renal revascularization; a mesenteric revascularization; or an arteriovenous access procedure. In some embodiments, the medical procedure is an invasive procedure. In some embodiments, the medical procedure is a diagnostic procedure.

In some embodiments, the at least one associated characteristic is a blood flow characteristic, a location of one or more lesions or blockages, or a location of one or more interventional devices. In some embodiments, the additional patient-specific data includes at least one of: data from an angiogram; data from optical coherence tomography; data from an intravenous ultrasound; blood pressure data; coronary flow data; cardiac contractility data; a measurement of a plaque; a local heart viability; data showing whether an occlusion is total or subtotal; data relating to the patient's physiological state; data relating to myocardial wall motions; stent position data; or data from a percutaneous coronary intervention. In some embodiments, determining a correspondence between the additional patient-specific data and at least one of the three-dimensional anatomical model or the at least one associated characteristic includes determining a location of the anatomical model to which the additional patient-specific data may apply. In some embodiments, the display unit is located in a medical facility.

In some embodiments of the present disclosure, a computer-implemented method for automatically updating an anatomical model includes receiving a patient-specific anatomical model generated from noninvasive imaging data, receiving at least one characteristic associated with the anatomical model, transmitting a representation of the anatomical model and the at least one associated characteristic to a display device, receiving additional patient-specific data from an interventional procedure, determining a correspondence between the patient-specific data and the anatomical model, locating a discrepancy between the additional patient-specific data and at least one of the anatomical model or the at least one associated characteristic, updating at least one of the anatomical model or the at least one associated characteristic to reduce the discrepancy, and transmitting an updated representation of at least one of the anatomical model or the at least one associated characteristic to the display device.

In some embodiments, the at least one associated characteristic is a blood flow characteristic. In some embodiments, the computer-implemented method further includes modeling an intervention on the anatomical model, and transmitting a representation of the modeled intervention to the display unit. In some embodiments, the computer-implemented method further includes: generating at least one recommendation of an intervention on the patient based on at least one of the anatomical model or the at least one associated characteristic; and transmitting the at least one recommendation to the display unit. In some embodiments, the computer-implemented method further includes: periodically receiving refreshed additional patient-specific data from the interventional procedure; monitoring for a new discrepancy between the refreshed patient-specific data and at least one of the anatomical model or the at least one associated characteristic; and if a new discrepancy is found, updating at least one of the anatomical model or the at least one associated characteristic to reduce the new discrepancy, and transmitting an updated representation of at least one of the anatomical model or the at least one associated characteristic to the display device.

In some embodiments of the present disclosure, an anatomical modeling system includes a processor configured to receive a patient-specific, three-dimensional anatomical model of at least one cardiovascular vessel, receive at least one characteristic associated with the anatomical model, transmit a representation of at least one of the three-dimensional anatomical model or the at least one associated characteristic to a display unit, receive additional patient-specific data relating to the anatomical model from a medical procedure, determine a correspondence between the additional patient-specific data and at least one of the three-dimensional anatomical model or the at least one associated characteristic, identify a discrepancy between the patient-specific data and at least one of the three-dimensional anatomical model or the at least one associated characteristic, modify at least one of the three-dimensional anatomical model or the at least one associated characteristic to reduce the discrepancy, and transmit an updated representation of at least one of the three-dimensional anatomical model or the at least one associated characteristic to the display unit.

In some embodiments, the processor is further configured to: periodically receive refreshed additional patient-specific data from the interventional procedure; monitor for a new discrepancy between the refreshed patient-specific data and at least one of the three-dimensional anatomical model or the at least one associated characteristic; and if a new discrepancy is found, update at least one of the three-dimensional anatomical model or the at least one associated characteristic to reduce the new discrepancy, and transmit an updated representation of at least one of the three-dimensional anatomical model or the at least one associated characteristic to the display device. In some embodiments, the at least one associated characteristic is a blood flow characteristic. In some embodiments, the processor is further configured to generate a model of an intervention on the anatomical model, and transmit a representation of the modeled intervention to the display unit. In some embodiments, the processor is further configured to generate at least one recommendation of an intervention on the patient based on at least one of the three-dimensional anatomical model or the at least one associated characteristic, and transmit the at least one recommendation to the display unit.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

The present disclosure is directed to anatomical modeling using information from a medical procedure, such as coronary anatomical modeling using information from a diagnostic or interventional coronary procedure. In addition, the present disclosure is directed to modeling interventional treatments using information from a medical procedure. Additionally, the disclosure may include a system and method for monitoring anatomical and/or physiological changes that occur during a treatment procedure (e.g., as a result of placing a stent or bypass) and updating an anatomical and/or physiological model to reflect the changes. Treatment recommendations and/or treatment rankings may also be updated in response to updates to a patient anatomical and/or physiological model to help a physician make decisions in treating a patient.

More specifically, the present disclosure is directed to systems and methods for providing an updated anatomical model and treatment options using anatomical data obtained via invasive or non-invasive medical procedures. The presently-disclosed systems and methods may receive patient information (e.g., via medical imaging performed on the patient), generate a patient-specific geometry of vessels, blood flow, and/or pathologies based on the patient information, and update such patient-specific geometry based on additional images, measurement or data obtained during a medical procedure. Additionally, the presently-disclosed systems and methods may model interventional procedures on updated patient-specific geometry, and/or may provide recommended treatment options based on updated patient-specific geometry and/or modeled interventional procedures on updated patient-specific geometry.

For example, according to the present disclosure, an initial anatomical model may be generated or obtained using, for example, non-invasive imaging, a correspondence may be determined between the initial model and additional data and/or measurements that are obtained during a subsequent invasive or noninvasive procedure, the initial model and the additional data may be reviewed for discrepancies between the model and the additional data, and if a discrepancy is found, the anatomical model may be updated to incorporate the additional data and reduce the discrepancy. Such a method, and a system for performing such a method, may benefit cardiologists and other medical professionals who diagnose, plan, and perform treatments for patients with suspected diseases.

As another example, according to the present disclosure, an anatomical model is generated or obtained using, for example, non-invasive imaging, an intervention is performed on a patient at a site relevant to the anatomical model, additional data and/or measurements are obtained during and/or after the intervention that reflect one or more changes caused by the intervention at the site relevant to the anatomical model, and the anatomical model is updated to incorporate the changes caused by the intervention.

As a further example, according to the present disclosure, a system and method may be developed for providing an updated anatomical model, one or more modeled interventional procedures, one or more recommended procedures based on the updated anatomical model, and/or one or more modeled interventional procedures to a physician or other medical professional during a medical procedure, using information obtained during the medical procedure, such that the physician or other medical professional may have access to such an updated anatomical model, models of interventional procedures based on an updated anatomical model, and/or recommended procedures based on an updated anatomical model while performing an interventional procedure.

Figure 1:
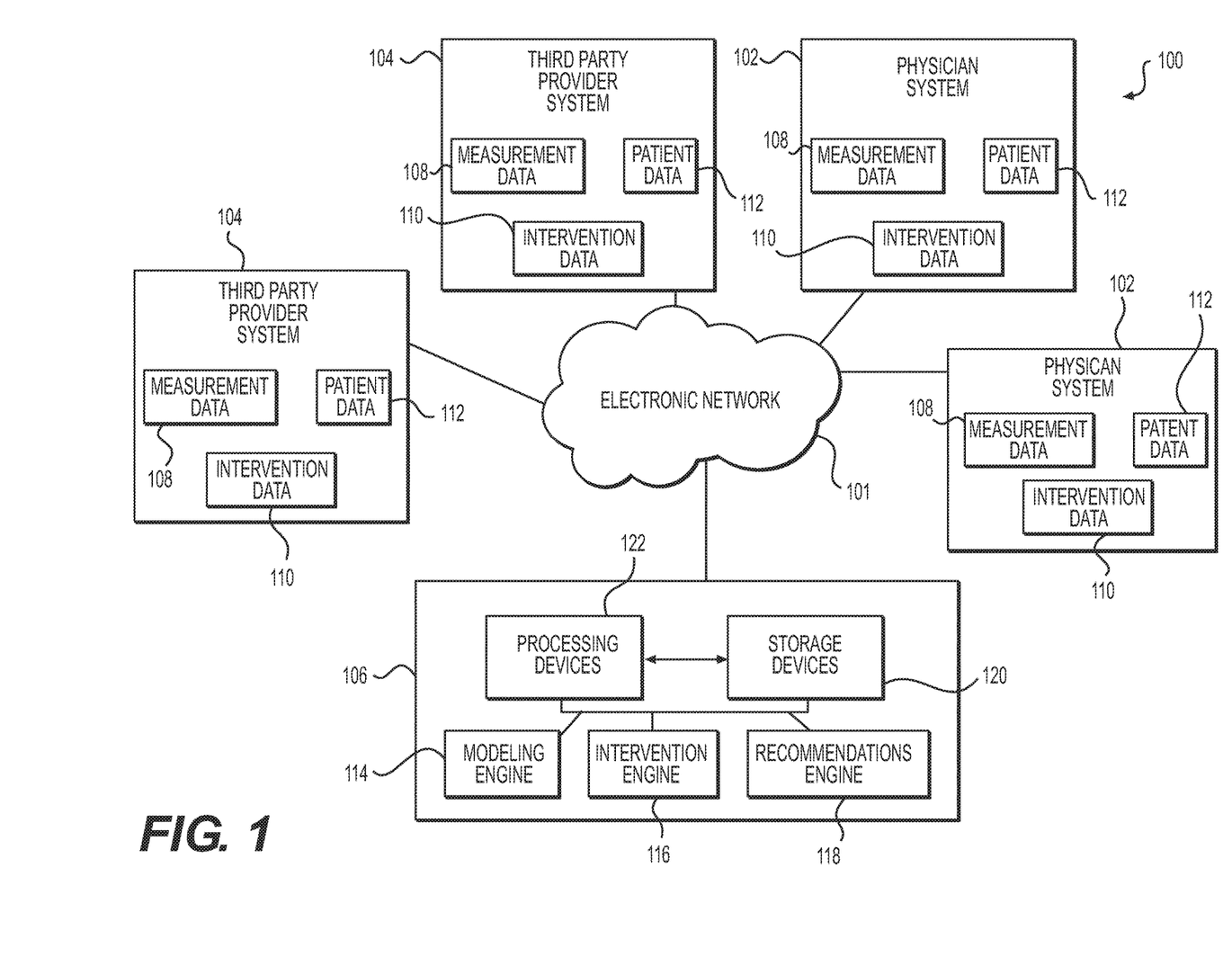
FIG. 1 depicts a schematic diagram of an exemplary system and network for creating and updating an anatomical model using information from a medical procedure.

Referring now to the figures, FIG. 1 depicts a high-level schematic diagram of an exemplary system and network for anatomical modeling using information from a medical procedure. Specifically, FIG. 1 depicts a plurality of physician systems 102 and a plurality of third party provider systems 104, any of which may be connected to an electronic network 101. Electronic network 101 may be, for example, a wired or wireless network of computer processors, electronic storage devices, etc., such as the Internet, a local area network, a wide area network, or any other computer network configuration known in the art. The plurality of physician systems 102 and third party systems 104 may house various types of data such as, for example, measurement data 108, intervention data 110, and patient data 112. Such categories of data may be related to a particular anatomical site in the human body, such as the heart, and/or a particular system of the human body, such as the cardiovascular system, and/or a portion of a particular system of the human body, such as the heart and adjacent vasculature.

One or more server systems 106 may also be connected to the electronic network 101, and may include various electronic devices and processors for storing, creating and manipulating images and data received, for example, over the electronic network 101 from physician systems 102 and/or third party systems 104. Server systems 106 may include, for example, storage devices 120 for storing images and data, and processing devices 122 for processing and manipulating images and data stored in the storage devices 122. Server systems 106 may also include a modeling engine 114 which may create and/or update an anatomical model using images and data received over the electronic network 101 and/or stored in storage devices 120 and/or processed in processing devices 122, as described further below. Server systems 106 may also include, for example, an intervention engine 116, which may model potential interventional procedures on an anatomical model generated and/or updated by modeling engine 114, and a recommendations engine 118 which may generate and/or update one or more recommendations of medical procedures based on an anatomical and/or physiological model generated and/or updated by modeling engine 114 and/or intervention engine 116. Any of the devices and engines in the server systems 106 may also send and/or receive data over the electronic network 101.

More specifically, physician systems 102 may include, for example, systems which collect and store data and medical records at medical offices, hospitals, and/or medical clinics, and diagnostic machines and systems used by physicians. Examples of physician systems 102 which may collect data include heart rate and blood pressure monitors, blood analysis equipment, electrocardiogram (ECG) machines, magnetic resonance imaging (MRI) machines, computed tomography (CT) machines, PET scanners, SPECT scanners, OCT machines, IVUS machinery, pressure wires, and other imaging devices. Examples of physician systems 102 which may store data include physician patient databases, computers, electronic patient management systems, and medical records keeping systems.

Third party provider systems 104 may include, for example, systems storing data and medical records at additional institutions, e.g., systems managed by diagnostic laboratories, academic institutions, insurance companies, medical instrument and/or implant manufacturers, etc. Third party provider systems 104 may also include imaging devices and/or laboratory equipment. Physician systems 102 and/or third party provider systems 104 may collect data from, for example, patient appointments, patient examinations, medical imaging, medical records, medical interventions, questionnaires, laboratory tests, insurance records, product catalogues, and medical databases.

Measurement data 108 of physician systems 102 and/or third party provider systems 104 may include data taken invasively and/or noninvasively from a patient using medical measurement devices, such as two- and three-dimensional images of patent anatomy obtained via, for example, CT scans, MRI procedures, PET scans, SPECT scans, and/or CCTA. CCTA may be used for imaging of patients with chest pain and involves using CT technology to image the heart and the coronary arteries following an intravenous infusion of a contrast agent. Additional data taken from a patient using medical measurement devices may include, for example, blood pressure, blood viscosity, heart rate, ECGs, platelet count, red blood cell count, biomarker evaluations, treadmill tests, echocardiography, angiograms, pressure wire measurements, OCT images and/or data, IVUS images and/or data, flow meter measurements, intravascular optical imaging, external cameras in an interventional suite/operating room, etc.

Intervention data 110 of physician systems 102 and/or third party provider systems 104 may include any data obtained around or during a medical procedure, e.g., interventions, such as intervention approach procedures, appropriate loci for an intervention, indications for an intervention, the number of times an intervention has been performed on a patient and/or on a population of patients, success rates, cost, risk factors, methods of performing an intervention, size and/or shape of intervention tools, e.g., stents, wires, and the like, etc.

Patient data 112 of physician systems 102 and/or third party provider systems 104 may include additional information about a patient, such as age, sex, weight, race, ethnicity, height, family medical history, medical records, etc.

Physician systems 102 and/or third party provider systems 104 may transmit, e.g., any of the above-described data to one another and/or to server systems 106 over the electronic network 101. Server systems 106 may be one or more computer processors and/or storage devices, which may be interconnected via one or more wired or wireless electronic connections. Server systems 106 may store data, including, e.g., images, received from physician systems 102 and/or third party provider systems 104 in one or more storage devices 120.

Storage devices 120 may be one or more computers, computer processors, hard drives, cloud-based storage systems, and/or other system configured to electronically store data and/or images. Storage devices 120 may store received data in, for example, one or more databases, digital file systems, and/or cloud-based storage systems. Further, the server systems 106 may process received data in one or more processing devices 122. Processing devices 122 may process data by, for example, cataloguing received data, sorting data by one or more categories, such as by patient, anatomical feature, intervention, measurement device, date created, date received, etc. Such processing may also include analyzing data and/or selecting data to send to modeling engine 114, intervention engine 116, and/or recommendations engine 118. Storage devices 120 and/or processing devices 122 may send received data, before or after it is stored and/or processed, to the modeling engine 114, the intervention engine 116, and/or the recommendations engine 118.

Storage devices 120, processing devices 122, modeling engine 114, invention engine 116, and recommendations engine 118 may each or all be, for example, one or more computer processors, computer storage devices, and/or combinations thereof. The modeling engine 114 may generate and/or update a three-dimensional anatomical model using relevant data received from the storage devices 120 and/or processing devices 122, via methods that are described in further detail below. The intervention engine 116 may model an intervention on a three-dimensional anatomical model using relevant data received from the storage devices 120 and/or processing devices 122, and/or using an anatomical model created or updated by the modeling engine 114, via methods that are also described in further detail below. The recommendations engine 118 may generate one or more recommended interventions based at least in part on the data received from the storage devices 120 and/or the processing devices 122, the anatomical model created or updated by the modeling engine 114, and/or one or more interventions modeled by the intervention engine 116.

Modeling engine 114, intervention engine 116, and recommendation engine 118 may all be located on any hardware capable of allowing them to perform the functions described herein. For example, the modeling engine 114, intervention engine 116, and recommendation engine 118 may all operate on a single computer, or may be a set of networked computers, working, for example, in series or in parallel. In further embodiments, the functions of the modeling engine 114, intervention engine 116, and recommendation engine 118 may be shared by two computational machines, or four or more computational machines.

Figure 2:
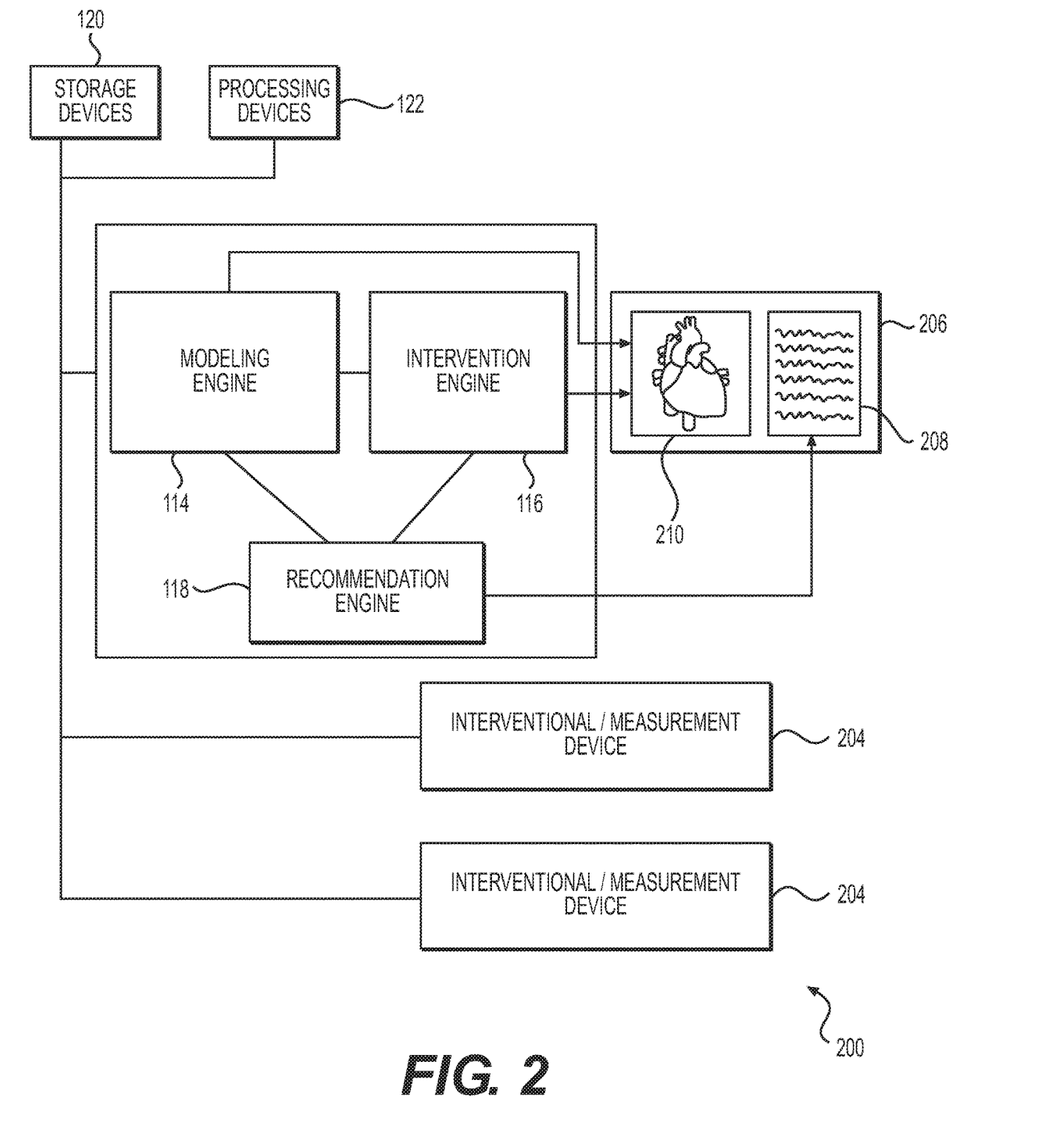
FIG. 2 depicts a more detailed schematic diagram of an exemplary system and network for creating and updating an anatomical model using information from a medical procedure.

FIG. 2 is another schematic diagram of an exemplary system 200 for generating and/or updating an anatomical model using data from a medical procedure. The system 200 may include, for example, storage devices 120 and processing devices 122, which may be configured to send data and images to the modeling engine 114, intervention engine 116 and recommendation engine 118, all of which may be interconnected via one or more wired or wireless connections (e.g., through an electronic network 101). One or more interventional and/or measurement devices 204 may also be connected to the storage devices 120, processing devices 122, modeling engine 114, intervention engine 116 and/or recommendation engine 118. The modeling engine 114, intervention engine 116 and/or recommendation engine 118 may also be electronically connected, via a wired or wireless connection, to at least one terminal 206. The terminal 206 may include a model display 210, and a recommendations display 208. In some embodiments, the system 200 may include one or more server systems 106.

Interventional and/or measurement devices 204 may be any medical devices configured to perform an intervention on, and/or take measurements and/or readings from, a patient. For example, interventional devices may include, e.g., endoscopic devices, laparoscopic devices, stents, prosthetic implants (e.g., prosthetic valves), grafts, and needles. Examples of measurement devices may include, e.g., image intensifiers, angiograms, pressure wires, OCT devices, IVUS devices, near-infrared spectroscopy (NIRS) devices, Raman spectroscopy (RS) devices, Doppler wire, flow meters, ultrasound devices, intravascular optical imaging devices, heart rate and blood pressure monitors, blood analysis equipment (e.g., equipment for measuring blood viscosity, platelet count, red blood cell count, and/or biomarkers), electrocardiogram (ECG) machines, magnetic resonance imaging (MRI) machines, computed tomography (CT) machines, PET scanners, SPECT scanners, echocardiography machinery, treadmill test equipment, and/or external cameras in an interventional suite or operating room. Interventional and/or measurement devices 204 may also be or include one or more computer processors, which may assist in taking and/or recording measurements, and/or transmitting measurements to storage devices 120, processing devices 122, modeling engine 114, interventions engine 116 and/or recommendations engine 118. Interventional and/or measurement devices 204 may be added to or removed from the system as needed.

Terminal 206 of system 200 may be located, for example, at the site of a medical procedure, or in a physician's office, hospital, examination room, or other location. Terminal 206 may include, for example, a computer processor and at least one display screen, such as a television, computer screen, tablet screen, or other mobile device screen. In some embodiments, terminal 206 may be located adjacent to a patient for whom anatomical modeling is being used to diagnose and/or treat the patient. In further embodiments, terminal 206 may be located in a physician office. In still further embodiments, terminal 206 may be a web browser-based terminal, and may be accessible via a user on, e.g., a personal computer. In such embodiments, the browser-based terminal may be secure, and may require, e.g., login or other credentials to be viewed. In further embodiments, system 200 may include more than one terminal 206, each terminal 206 being located at a different location (e.g., one may be located adjacent to a patient; another may be located in a physician office; another may be a browser-based terminal, etc.).

The model display 210 may be, for example, a visual display of a model received from the modeling engine 114 and/or the intervention engine 116. In some embodiments, the model display 210 may be a two-dimensional visual representation of a three-dimensional model. In some embodiments, the model display 210 may be manipulable from terminal 206 or from elsewhere. For example, a user, such as a physician, may use a keyboard, mouse, or touchscreen input to rotate, zoom in on, zoom out on, or view details on parts of, the model display 210. In some embodiments, various characteristics and measurements may be labeled in text form on the model display 210, such as, for example, one or more blood flow characteristics, the location of one or more lesions or blockages, and/or the location of one or more interventional devices, e.g., stents, prosthetic valves, grafts, etc. In some embodiments, the model display may be, for example, within a digital window on a screen of terminal 206. In further embodiments, the model display 210 may be on, for example, a discrete screen that is a part of terminal 206, and that is separate from, e.g., a recommendations display 208 screen.

The recommendations display 208 may be, for example, a visual display of one or more recommendations for medical treatments received from the recommendation engine 216. In some embodiments, for example, the recommendations display may be a list of one or more recommendations for interventions. In such embodiments, the recommendations display may show, for each entry in the list, the type of intervention being recommended and/or the name of the site for which the intervention is recommended. In some embodiments, the recommendations display may also show what intervention materials (e.g., a stent or other implant) are needed. In some embodiments, the recommendations display may be a digital window display located adjacent to the model display 210. In further embodiments, the recommendations display may be integrated into the model display 210, and may display a model of one or more recommended interventions, generated, e.g., by interventions engine 116, on the model display 210. In further embodiments, the recommendations display may include, for example, a selectable list of one or more recommendations for interventions, each of which, upon being selected, may be displayed in a visual model on model display 210.

Figure 3:
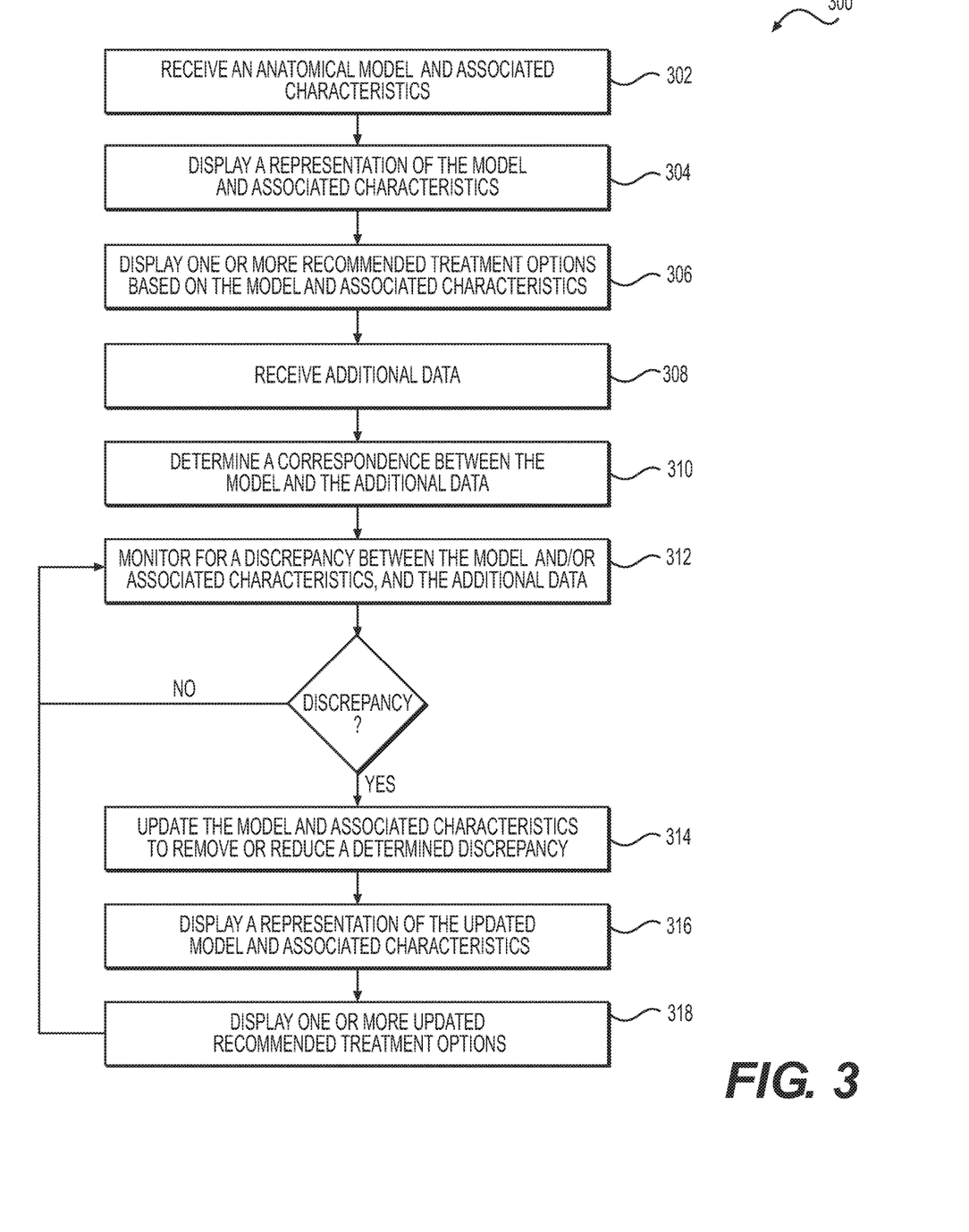
FIG. 3 depicts a flow diagram of an exemplary method for creating and updating an anatomical model using information from a medical procedure.

One embodiment of the present disclosure uses patients' cardiac imaging to derive a patient-specific anatomical model of the patient's heart, vasculature, and/or features thereof, and update the geometric model using additional data received from one or more interventional and/or measurement devices. For example, FIG. 3 depicts a block diagram of an exemplary method 300 of anatomical modeling using information from a procedure. The exemplary method depicted in FIG. 3 may be performed, for example, by server systems 106. Specifically, as shown in FIG. 3, one method 300 for anatomical modeling using information from a medical procedure includes receiving an anatomical model and associated characteristics in, e.g., electronic form (step 302). Method 300 may further include displaying a representation of the model and associated characteristics (step 304). Method 300 may further include displaying one or more recommended treatment options based on the model and associated characteristics (step 306). Such recommended treatment options may, for example, be generated by recommendations engine 118, and may be displayed on a recommendations display 208 adjacent to the display of the model 210, on the terminal 206. Method 300 may also include receiving additional data (step 308), such as additional measurements, patient-specific data, and/or interventional data from one or more interventional and/or measurement devices 204. Method 300 may further include determining a correspondence between the model and the additional data (step 310). Such a correspondence may include, for example, relating one or more points of additional data to one or more aspects of the model. Method 300 may further include monitoring for a discrepancy between the model and associated characteristics and the additional data (step 312). Such a discrepancy may be, for example, a mismatch between one or more points of additional data and a corresponding aspect of the model. If a discrepancy is not found, the monitoring step may be continued. If a discrepancy is found, then the model and associated characteristics may be updated to remove or reduce the discrepancy (step 314). Updating the model and associated characteristics may include, for example, adjusting an aspect of the model corresponding to one or more points of additional data for which a discrepancy was detected. Method 300 may further include displaying a representation of the updated model and associated characteristics (step 316), for example, on the terminal 206. Method 300 may further include displaying one or more updated recommended treatment options to be displayed (step 318). Such updated recommended treatment options may be obtained from, for example, recommendations engine 118, which may generate the updated treatment options based at least in part on the updated model and/or associated characteristics. Monitoring step 312 may be repeated during or completion of the display of a representation of the updated model and/or updated recommended treatment options.

Method 300 will now be described in more detail below with reference to FIG. 3, including specific exemplary characteristics and exemplary steps.

In one embodiment, the anatomical model and associated characteristics received according to step 302 may be, for example, a patient-specific model of at least a portion of a system, such as a cardiovascular system. For example, the anatomical model may include a representation of any vascular system, anatomy, or subsystem, including, for example, coronaries, carotids, cerebral vessels, peripheral vessels, renal vessels, visceral vasculature, aorta, inner and outer vessel walls, plaque compositions, the left ventricle myocardium, the entire heart, muscle tissue, and/or organ tissue. The anatomical model may represent various patient-specific aspects of a system, such as a patient-specific geometry of any of the above systems, anatomies, or subsystems. Such a geometry may be represented as a list of points in space (possibly with a list of neighbors for each point) in which the space can be mapped to spatial units between points (e.g., millimeters). In one embodiment, the anatomical model may be, for example, a three-dimensional model.

Associated characteristics received according to step 302 may include, e.g., one or more estimates of, or known, physiological or phenotypic parameters of the patient, such as for example, patient age or patient gender. Associated characteristics may also include one or more blood flow characteristics, cardiovascular risks, and/or biomechanical characteristics at one or more locations in the anatomical model. Examples of such characteristics and/or risks include fractional flow reserve (FFR), coronary flow reserve (CFR), pressure, flow rate, flow velocity, axial plaque stress, wall shear stress, oscillatory shear index, plaque force, heart function (e.g., stroke volume, ejection fraction, etc.), wall motion, heart, muscle, or organ perfusion, heart electrophysiology characteristics (e.g., electrical propagation), plaque rupture risk, myocardium risk, cardiac and/or tissue perfusion, likelihood of progression or regression of plaques, likelihood of complications, and/or pulsatile flow. Associated characteristics may be received from, e.g., physician systems 102, third party systems 104, storage devices 120, and/or processing devices 122, and/or may be generated by the modeling engine 114 and/or the interventions engine 116 using a generated anatomical model.

Associated characteristics may also be determined by calculations based on the received anatomical model. For example, a characteristic such as a blood flow characteristic may be determined by performing, with the anatomical model, a three-dimensional blood flow simulation, reduced order model blood flow simulation (e.g., a one-dimensional blood flow simulation), a finite elements calculation, a biomechanical simulation, an electrophysiological simulation, estimation of simulated quantities and/or risks using machine learning from a database, etc.

The anatomical model and associated characteristics may be generated and/or updated by, for example, modeling engine 114, using data (e.g., images) stored in storage devices 120, data processed by processing devices 122, and/or any measurement data 108, intervention data 110, and/or patient data 112 received from one or more physician systems 102 and/or third party provider systems 104. For example, the modeling engine 114 may receive data from storage devices 120, processing devices 122, physician systems 102, and/or third party systems 104, and may construct a patient-specific anatomical model and determine associated characteristics using that received data. In some embodiments, such data may include, for example, images of a patient's anatomy obtained noninvasively by, for example, a CT or CCTA procedure, an MRI, or any other noninvasive procedure. In one embodiment, such data may be CCTA data, and may be a set of images and/or data relating to a number of "slices" or cross-sections of a patient's heart. The modeling engine 114 may then construct a three-dimensional image of the patient's heart using the received slices. The modeling engine 114 may further run an FFR-CT (fractional flow reserve-computed tomography) analysis on the three-dimensional image in order to further construct an anatomical model of the patient's heart, and/or generate one or more associated characteristics for the anatomical model. A FFR-CT analysis is more thoroughly discussed in, for example U.S. Pat. No. 8,315,812, filed on Jan. 25, 2011 by Charles A. Taylor, which is incorporated herein by reference in its entirety. The modeling engine 114 may alternatively or additionally run a CPR (curved planar reformation) analysis on the three-dimensional image in order to further construct an anatomical model of the patient's heart, and/or generate one or more associated characteristics for the anatomical model.

Alternatively, other noninvasive imaging methods, such as magnetic resonance imaging (MRI) or ultrasound (US), or invasive imaging methods, such as digital subtraction angiography (DSA), may be used to produce images of the structures of the patient's anatomy. The imaging methods may involve injecting the patient intravenously with a contrast agent to enable identification of the structures of the anatomy. The resulting imaging data (e.g., provided by CCTA, MRI, etc.) may be provided from a third-party system 104, such as a radiology lab or a cardiologist, or by the patient's physician system 102, etc. The image data may be stored by storage devices 120 and/or processed by processing devices 122, as well as being received by modeling engine 114. Methods of creating such a model and determining associated characteristics are more fully described in, for example, U.S. Pat. No. 8,315,812, which is incorporated herein by reference in its entirety. The anatomical model may be received, for example, in an electronic storage medium, such as a digital file or plurality of digital files.

Displaying the representation of the model according to step 304 may include, for example, displaying a representation of the model on model display 210 of terminal 206. In some embodiments, the representation of the model may be a visual representation of the model as viewed from a desired angle and/or cross-section using, for example, three-dimensional rendering, coloring, shading, plots, etc. In some embodiments, the visual representation may include a three-dimensional rendering of the anatomical model, including, for example, a lumen surface, outer wall surface, plaque, plaque composition, occlusions, heart, myocardial tissue, and/or other muscles or organs. In some embodiments, the representation of the anatomical model may be manipulable via an input method. For example, terminal 206 may be equipped with a keyboard, mouse, touch-screen interface or other hardware configured to receive user input, and the representation of the anatomical model on the model display 210 may be rotated, enlarged, shrunken, or viewable from various cross-sections. In another embodiment, displaying a representation of the anatomical model may include displaying the model from multiple angles, either simultaneously or in sequence. In another embodiment, the representation displayed according to step 304 may be a simplified version of the anatomical model, e.g., a simplified diagram, a schematic representation, and/or combinations thereof.

The associated characteristics displayed according to step 304 may be, for example, any of the associated characteristics received according to step 302, and/or any associated characteristics generated by modeling engine 114 and/or intervention engine 116. The associated characteristics may be displayed as an integrated part of the model, e.g., on the model display 210, and/or as annotations to the representation of the anatomical model, and/or as a list separate from the anatomical model, either on the model display 210 or on a separate screen at, for example, terminal 206. For example, the location, size, and shape of a plaque in a coronary anatomical model may be represented by a geometry on the representation of the anatomical model. As another example, vessel injury may be represented by a marking on the portion of the representation of the anatomical model corresponding to the site of injury, potentially in combination with an annotation and text describing the type of injury. As further examples, Reynolds numbers, Wolmsley numbers, and/or local flow rates may be represented by annotations on the model at the site to which they apply; alternately, one or more such characteristics may be represented by a list separate from representation of the model on model display 210.

The recommended treatment options displayed according to step 306 may vary depending at least on the received anatomical model and associated characteristics. Potential treatment options may include, for example, a possible stent location, bypass location, a rotablation, atherectomy, angioplasty, endarterectomy, PCI, coronary artery bypass grafting (CABG), carotid and/or peripheral intervention, renal and/or mesenteric revascularization, arteriovenous access procedures, location of pacemaker leads, ablation sites, etc.

In some embodiments, the recommended treatment options may be generated by, for example the recommendation engine 118, based on a plurality of potential treatment options received from one or more sources, such as, for example, physician systems 102, third-party systems 104, storage devices 120, processing devices 122 and/or intervention engine 116, any of which may store a plurality of treatment options, such as medications, surgical procedures, and/or diagnostic procedures. Each treatment option may be associated with one or more types of intervention data, such as indications for the treatment option, risk factors, cost, probability of success, and/or any intervention data 110 that may have been received from a physician system 102 or a third-party system 104.

In some embodiments, the recommendation engine 118 may receive an anatomical model and associated characteristics from the modeling engine 114, and may generate a list of recommended treatment options based on a plurality of potential treatment options, the received anatomical model, and/or the associated characteristics. The recommended treatment options may correspond to particular characteristics in the anatomical model, which the recommendation engine 118 may categorize as being of interest. For example, the recommendation engine 118 may recognize a lower-than-optimal blood flow rate represented at a given locus in the anatomical model, and may generate a recommended treatment option having intervention data indicating that the treatment option is designed to increase blood flow rate at the given locus. As another example, the recommendation engine 118 may recognize the build-up of plaque at a location in the anatomical model, and may add one or more recommended treatment options designed to remove the plaque.

In some embodiments, the recommendation engine 118 may determine a recommended treatment option by querying the intervention engine 116 to generate an intervention model and associated characteristics of a potential treatment option, based on the anatomical model received according to step 302. The intervention engine 116 may model, for example, the potential treatment option on the received anatomical model, and may calculate one or more changes to associated characteristics of the received anatomical model based on its generated model of the potential treatment option on the received anatomical model. The recommendation engine 118 may analyze the generated intervention model and associated characteristics to determine whether the potential treatment results in an improvement to the anatomical model, and based on its analysis, may or may not designate the potential treatment option as a recommended treatment option.

In further embodiments, the recommendation engine 118 may evaluate one or more potential treatment options based on intervention data associated with the potential treatment option, such as the level of risk posed to the patient, the success rate of the treatment, etc. The recommendation engine 118 may also evaluate one or more potential treatment options based on a combination of any of the above analyses of the potential treatment options.

In yet further embodiments, one or more treatment options may be generated by a fully or partially automated system, such as those described in, for example, U.S. Pat. No. 9,449,146, filed on Jul. 3, 2014 by Ryan Spilker et al., or U.S. Pat. No. 9,043,190, filed on Apr. 16, 2014 by Leo Grady et al, both of which are incorporated by reference herein in their entireties. In some embodiments, recommendation engine 118 may include one or more such fully or partially automated systems.

In further embodiments, one or more treatment options may be suggested or desired by a physician or other medical professional, and may be manually added to the one or more recommended treatment options.

The recommended treatment options may be displayed as an integrated part of the model displayed on terminal 206. For example, the representation of the anatomical model displayed according to step 304 may be overlaid with, or replaced by, a representation of one or more potential interventions on the anatomical model. The representation of one or more potential interventions on the anatomical model may be generated by, for example, intervention engine 116. Multiple recommended treatment options may be displayed on the representation of the anatomical model simultaneously, or may be displayed one at a time. In an alternate embodiment, recommended treatment options may be displayed separately, e.g., as a list of selectable entries on a recommendations display 208. In some embodiments, each selectable entry on the recommendations display 208 may be viewed on the anatomical model displayed on the model display 210 when selected.

In some embodiments, the recommended treatment options may be scored to reflect the optimality of each possible treatment. Optimality of a possible treatment may be based, for example, on patient data, such as the age of the patient, intervention data such as the success rate of the intervention, the ease of the intervention, stress factors on the patient, etc., and/or potential improvements to the anatomical model that may result from the possible treatment. For example, the intervention engine 116 may model a potential stent position in the anatomical model, and may calculate that the distal vessel would achieve an FFR greater than a cutoff of 0.8. The recommendation engine 118 may then score the potential stent position accordingly, and/or may rank the potential stent position among other potential treatment options in order of optimality. In some embodiments, the optimality of one or more recommended treatment options may be displayed along with the display of one or more recommended treatment options according to step 306. For example, the one or more recommended treatment options may be displayed according to step 306 in order of optimality.

Additional data received according to step 308 may be any additional data pertaining to the anatomical model, associated characteristics and/or the patient, including, for example, data received from one or more interventional and/or measurement devices 204. Additional data may relate to, for example, viewing angles of an image (e.g., an angiogram), lumen size at one or more locations in the anatomical model, pressure or FFR at a location, blood flow rate at a location, heart rate, cardiac contractility, plaque location or composition, wall motion, size and shape of a heart or other organ, necrosis or evidence of ischemia, electrical information (e.g., voltage, current, resistance, etc.), patient physiological state, heart function (e.g., stroke volume, ejection fraction, etc.), wall shear stress or axial plaque stress, force applied to a plaque, vessel wall, muscle, or organ, patient motion, bypass grafting, or any other characteristic relevant to the received anatomical model.

In some embodiments, an interventional and/or measurement device 204 may be configured to transmit additional data in the form of measurements, images, and/or other forms to the modeling engine 114, intervention engine 116, and/or recommendations engine 118. For example, an interventional and/or measurement device 204 may be configured to transmit measurements, images, and/or other data to a physician system 102 or a third party provider system 104 (as depicted in FIG. 1), which may then transmit the data to modeling engine 114, intervention engine 116, and/or recommendations engine 118, e.g. over an electronic network 101. In still further embodiments, an interventional and/or measurement device may be configured to transmit measurements, images, and/or other data to a physician system 102 or a third party provider system 104 (as depicted in FIG. 1), which may then transmit the data to a processing device 120 and/or a storage device 122 (e.g. over an electronic network 101), which may then transmit the data to modeling engine 114, intervention engine 116, and/or recommendations engine 118.

In still further embodiments, a physician or other practitioner may take down data and/or measurements received from an intervention and/or measurement device onto a device, such as a computer, that is part of a physician system 102, which may then transmit such data and/or measurements to one or more of a storage device 120, processing device 122, modeling engine 114, intervention engine 116, and/or recommendations engine 118.

Determining a correspondence between the model and the additional data according to step 310 may be performed by, for example, a processing device 122, a modeling engine 114, and/or an intervention engine 116. Determining a correspondence may include, for example, identifying a feature or features of the anatomical model and/or associated characteristics that are affected by the additional data. In some embodiments, the correspondence may be determined by performing a registration of the additional data to a site of, or additional characteristic of, the received anatomical model. For example, a physician, an interventional and/or measurement device 204, processing device 122, modeling engine 114, and/or intervention engine 116 may assign a locus to the additional data, the locus corresponding to a position on the received anatomical model. In further embodiments, the correspondence may be determined by knowing the distance of an interventional and/or measurement device 204 used to take the additional data from a landmark in the anatomical model (e.g., the distance of a pressure wire from the aortic ostium).

In some embodiments, multiple types of additional data may be received from one or more interventional and/or measurement devices 204 or other sources. For example, additional data may be received from, e.g., both a pressure wire and an angiogram. In such embodiments, the step of determining a correspondence between the received anatomical model and the additional data may be performed for each type of additional data.

Monitoring for a discrepancy between the anatomical model and associated characteristics and the additional data according to step 312 may be performed by, for example, the modeling engine 114, the intervention engine 116, and/or the processing devices 122. A discrepancy may be, for example, a mismatch between one or more points of additional data and the configuration of the received anatomical model, based on the correspondence determined between the additional data and the anatomical model. The monitoring step 312 may be continued throughout, for example, an intervention or diagnostic procedure. In embodiments where multiple types of additional data are received, the monitoring step 312 may be performed with respect to each type of additional data and the anatomical model. The monitoring step may be performed intermittently or continuously, and may be performed while simultaneously performing any of the other steps of method 300, e.g., steps 314-318.

Updating the model to remove a discrepancy according to step 314 may include a variety of changes to the model depending on the discrepancy found. For example, if additional data received from, e.g., an angiogram, OCT, or IVUS results in detection of a discrepancy of a lesion size compared to a lesion size in the received anatomical model, the anatomical model may be updated to reflect the lesion size detected invasively.

As a further example, if additional data in the form of a blood pressure measurement from a pressure wire is different from a blood pressure shown in the received anatomical model, then the anatomical model may be updated to include the blood pressure measured by the pressure wire.

As another example, if additional data in the form of a coronary flow measurement detected or predicted by a Doppler wire is different from a coronary flow in the received anatomical model, the anatomical model may be updated to include the coronary flow measured or predicted by the Doppler wire.

As a further example, if additional data shows a cardiac contractility that differs from parameters used in the anatomical model, the anatomical model may be updated to include the measured cardiac contractility.

As yet another example, if additional data shows a measured plaque composition, size and/or shape that are different from a plaque composition, size and/or shape in the received anatomical model, then the plaque size, composition, shape, force calculations, rupture risk, predicted plaque progression or regression, and/or myocardium at risk in the anatomical model may be updated to reflect the measured plaque composition, size and/or shape received in the additional data.

As yet another example, if additional data shows a measured local heart viability that is different from a local heart viability in the received anatomical model, then local heart viability and electrophysiological predictions may be updated in the anatomical model to reduce the discrepancy.

As a further example, if additional data shows that a lesion modeled in the anatomical model as a total occlusion is in fact subtotal, then the boundary conditions and blood flow characteristics in the anatomical model may be recalculated.

As yet another example, if additional data reveals a patient physiological state (e.g., hyperemia, rest, etc.), then boundary conditions for the anatomical model may be updated and blood flow characteristics may be recalculated.

As still another example, if additional data relating to myocardial wall motion indicates loss of tissue viability, a difference in motion, or stiffness, then the anatomical model may be updated such that the heart function, perfusion estimation, electrophysiological parameters, and/or boundary conditions for a blood flow characteristic computation may be recalculated.

As another example, if a stent is deployed during an interventional procedure and additional data is received reflecting the stent deployment, then the anatomical model may be updated to reflect the presence of the stent by, for example, changing the pressure differences in an FFR-computed tomography calculation (FFR-CT).

As yet another example, if additional data received during, for example, a percutaneous coronary intervention (PCI) indicates FFR and lumen diameter values that are different from the FFR and lumen diameter values in the anatomical model, then the inputs of an FFR-CT calculation for an anatomical model may be adjusted to reduce the discrepancy. For example, an additional FFR-CT value may result in the percent stenosis over a vessel segment being retrofit.

Updating the associated characteristics may include, for example, determining a new or updated blood flow characteristic, biomechanical characteristic, and/or risk score based on the updated model. For example, an updated blood flow characteristic, biomechanical characteristic, and/or risk score may be calculated by performing, with the updated anatomical model, a three-dimensional blood flow simulation, reduced order model blood flow simulation (e.g., a one-dimensional blood flow simulation), a finite elements calculation, biomechanical simulation, electrophysiological simulation, estimation of simulated quantities and/or risks using machine learning from a database, etc.

Displaying a representation of the updated model and associated characteristics according to step 316 may be accomplished by, for example, any of the methods described above with respect to displaying the representation of the initial received model and associated characteristics according to step 304. Additionally, displaying a representation of the updated model may include, for example, matching a viewing angle provided by additional data, such as a viewing angle from an image intensifier or an angiogram.

One or more updated recommended treatment options to be displayed according to step 318 may be determined based on the updated anatomical model. Such updated recommended treatment options may be determined by, for example, recommendations engine 118, which may generate the updated treatment options based at least in part on the updated model and/or associated characteristics, as was described above with respect to step 306. For example, if additional data resulted in an updated lesion size, vessel size, or lesion composition in the anatomical model, then the recommendation engine 118 may recompute treatment options or equipment choices (e.g., catheter configuration, catheter shape choice, based on an updated aortic and/or coronary anatomy or configuration) based on the updated anatomical model. As a further example, the recommendation engine 118 may re-evaluate the optimality of one or more recommended treatment options based on an updated model. For example, if additional data reveals that a stent was placed in one of two serial lesions represented in an anatomical model, recommendation engine 118 may evaluate or reevaluate the benefit of placing a stent in the second serial lesion (e.g., optionally using intervention engine 116 to model the placement of a stent in the second serial lesion and the effect of the placement on one or more characteristics of an updated anatomical model, such as a blood flow characteristic).

The steps of method 300 may be performed iteratively, or may be performed simultaneously, repeatedly, and/or in real-time during, for example, an interventional or diagnostic procedure. In some embodiments, not all steps of method 300 may be performed. In further embodiments, a subset of steps of method 300 may be performed repeatedly, while other steps are performed only once or are not performed.

Figure 4A:
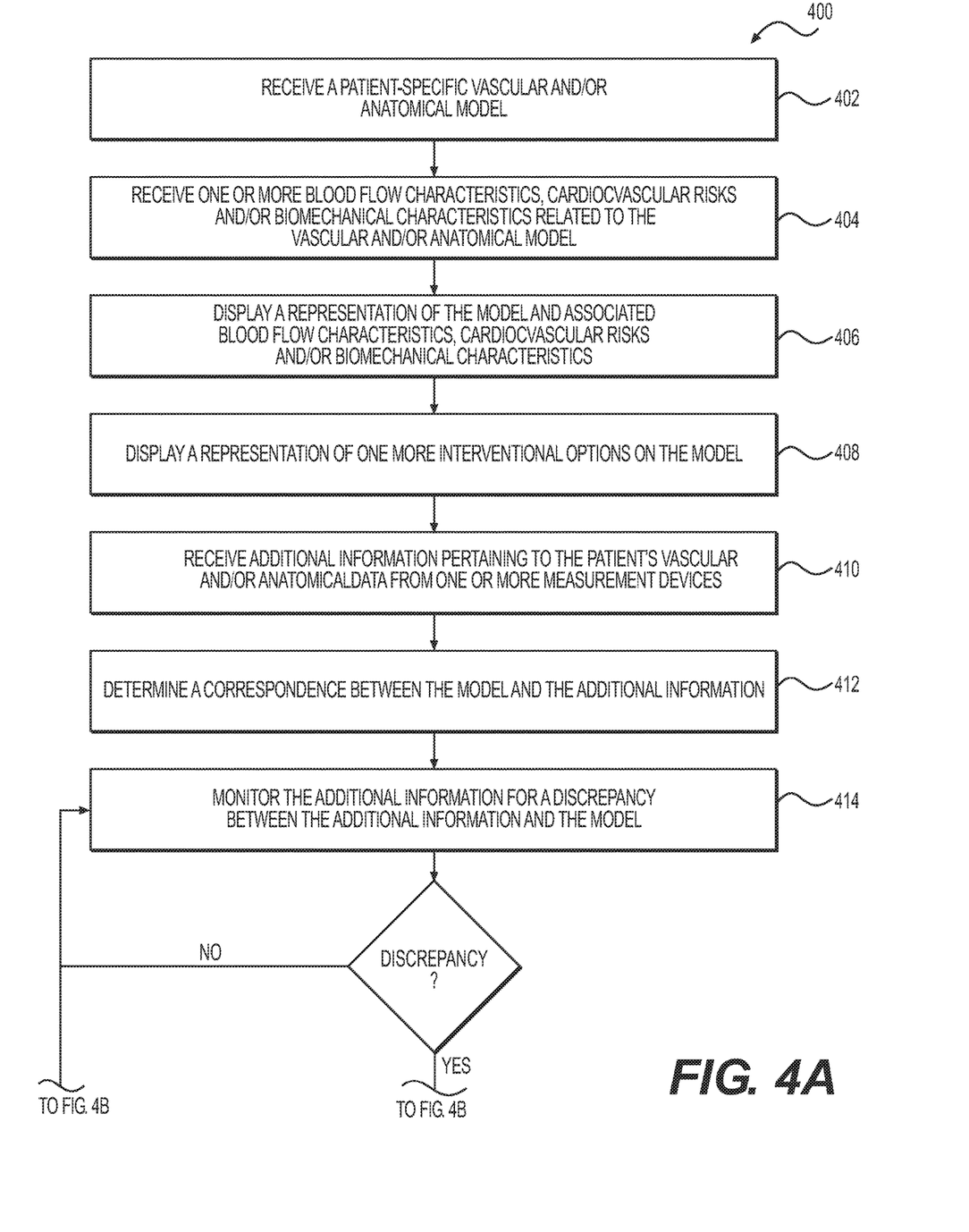
FIGS. 4A-4B depict a flow diagram of another exemplary method for creating and updating an anatomical model using information from a medical procedure.
Figure 4B:
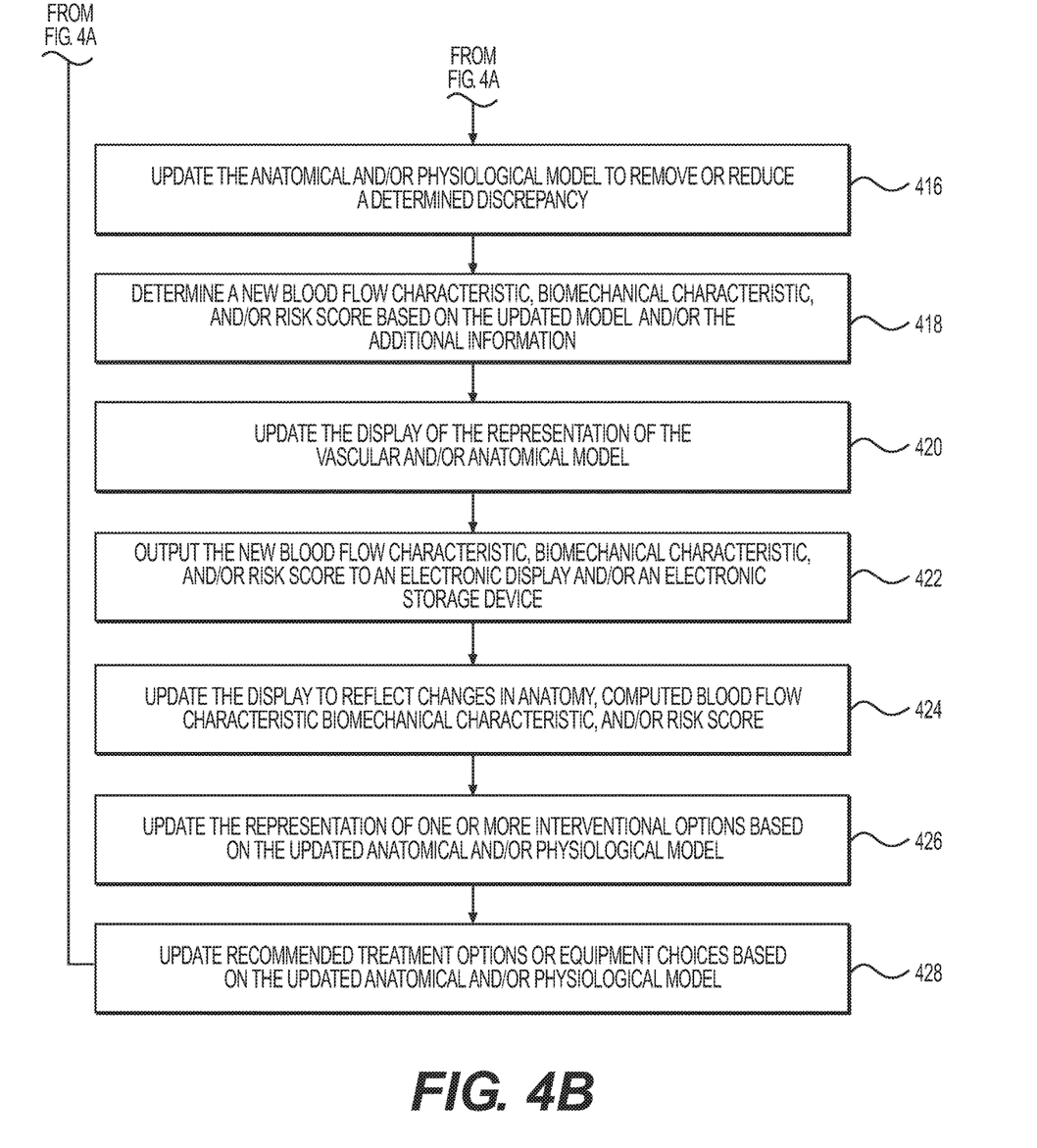

FIGS. 4A-4B depict a block diagram of a more detailed exemplary method 400 for anatomical modeling using information from a procedure. According to step 402, a patient-specific vascular and/or anatomical model may be received, for example, in an electronic storage medium. Such a vascular and/or anatomical model may be generated and/or updated by, for example, modeling engine 114 according to any of the methods described herein (e.g., using images from a CCTA), and/or may be retrieved from storage devices 120 and/or processing devices 122. According to step 402, one or more blood flow characteristics, cardiovascular risks and/or biomechanical characteristics related to the vascular and/or anatomical data may be received. Such blood flow characteristics, cardiovascular risks and/or biomechanical characteristics may be received from, for example, physician systems 102, third party provider systems 104, storage devices 120, and/or processing devices 122, and/or may be generated and/or calculated by modeling engine 114 using the vascular and/or anatomical model received according to step 402. For example, one or more blood flow characteristics may be computed by modeling engine 114 using an FFR-CT analysis on the anatomical model and/or images and/or data received from, for example, physician systems 102, third party provider systems 104, storage devices 120, and/or processing devices 122.

According to step 406, a representation of the model and associated blood flow characteristics, cardiovascular risks, and/or biomechanical characteristics may be displayed. Such a display may be according to, for example, any of the methods of display described herein with respect to method 300, e.g., using terminal 206, model display 210, and/or recommendations display 208. According to step 408, a representation of one or more interventional options may also be displayed on the model, using any of the methods previously described herein.

According to step 410, additional information pertaining to the patient's vascular and/or anatomical data may be received from one or more measurement devices. For example, additional information may be received from one or more interventional and/or measurement devices 204, as has been previously described herein. According to step 412, a correspondence between the model and the additional information may be determined, as has been previously described herein. According to step 414, the additional information and the model may be monitored for a discrepancy between the two, by, for example, modeling engine 114, processing devices 122, intervention engine 116, or other processor. Upon a discrepancy being discovered, then according to step 416, the model may be updated to remove or reduce the discrepancy by, for example, using modeling engine 114. According to step 418, a new blood flow characteristic, biomechanical characteristic, and/or risk score based on the updated model and/or additional information may be determined. For example, using the updated model, modeling engine 114 may run a new FFR-CT analysis using the updated model to obtain a new blood flow characteristic, biomechanical characteristic, and/or risk score. According to step 420, the display of the representation of the model on, for example, model display 208 of terminal 206 may be updated based on the updated model. According to step 422, the new blood flow characteristic, biomechanical characteristic, and/or risk score may be output to an electronic display and/or electronic storage device, such as, for example, terminal 206 or storage devices 120. According to step 424, the display (e.g., model display 210) may be updated to reflect changes in anatomy, a computed blood flow characteristic, biomechanical characteristic, and/or risk score. According to step 426, the representation of one or more interventional options may be updated based on the model by, for example, intervention engine 116. According to step 428, recommended treatment options or equipment choices may be updated based on the model. For example, recommendation engine 118 may generate or update a plurality of recommended treatment options or equipment choices based on, e.g., the updated model and/or a change in anatomy, blood flow characteristic, biomechanical characteristic, and/or risk score. More additional information may be received, according to step 414, to which steps 416-428 may be applied.

The steps of method 400 may be performed iteratively, or may be performed simultaneously, repeatedly, and/or in real-time during, for example, an interventional or diagnostic procedure. In some embodiments, not all steps of method 400 may be performed. In further embodiments, a subset of steps of method 400 may be performed repeatedly, while other steps are performed only once or are not performed.

In some embodiments, the steps of methods 300 and 400 may additionally allow a user, such as a physician or other medical professional, to store and/or retrieve one or more received anatomical models and/or associated characteristics, displayed recommended treatment options, updated anatomical models and/or associated characteristics, and/or updated recommended treatment options, using, for example, an input device in conjunction with terminal 206 such as a keyboard, mouse, and/or touch-screen interface.

In alternate embodiments, the functions of modeling engine 114, intervention engine 116, and recommendation engine 118 may not be split apart into separate discrete categories, but may instead be shared and performed by one or more computer processors.

An exemplary form of the disclosure herein will now be described. A patient-specific vascular and/or anatomical model in an electronic storage medium (e.g., a network drive, hard drive, cloud drive, mobile phone, tablet, etc.) may be received, showing a flow fractional reserve computerized tomography (FFR-CT) map and/or curved planar reformation (CPR) images of a plaque and/or vessel wall. One or more stents may then be introduced into the anatomy of the patient represented by the patient-specific vascular and/or anatomical model, in a position and sequence selected by a medical professional. The patient-specific vascular and/or anatomical model showing the FFR-CT map and/or CPR images may be displayed on an image screen, such as a computer monitor. The model may be updated as each stent is deployed to reflect the presence of the stent and its effect on the vasculature and/or anatomy represented in the model (e.g., changes in pressure differences in the FFR-CT map). The model may be rotated periodically on the display, and may be updated constantly and/or at each rotation of the model so that the model is synchronized with real-time physical changes (e.g., placement of the one or more stents). A list of procedural options to improve the quality and/or speed of a procedure, and/or the outcome of a procedure, may be provided in real-time during insertion of the one or more stents. This updating may include, but is not limited to, enabling a user to perform virtual stenting to predict stenting solutions, enabling a user to store, retrieve, and/or display stenting options, enabling a user to perform stent solutions at will during the course of a procedure, and/or updating a "current status" solution, which may be fixed after each new stent is deployed and in place.

Any aspect set forth in any embodiment described herein may be used with any other embodiment set forth herein. Every method step set forth herein may be performed by any single computer processor and/or server or combination of computer servers and/or processors, and may be completed local to a given location or remotely on any suitable computer processor, combination of computer processors, interactive display or displays, monitor(s) or screen(s).

It will be apparent to those skilled in the art that various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

We claim:

1. A method of automatically updating a cardiovascular model, comprising:
   using a processor to determine a correspondence between patient-specific data from a medical procedure and at least one of a patient-specific three-dimensional anatomical model of at least one cardiovascular vessel or at least one characteristic associated with the three-dimensional anatomical model;
   using the processor to identify a discrepancy between the patient-specific data and at least one of the three-dimensional anatomical model or the at least one associated characteristic;
   using the processor to modify at least one of the three-dimensional anatomical model or the at least one associated characteristic to reduce the discrepancy;

using the processor to transmit an updated representation of at least one of the three-dimensional anatomical model or the at least one associated characteristic to a display unit;
using the processor to generate at least one recommendation of an intervention on the patient based on at least one of the three-dimensional anatomical model or the at least one associated characteristic; and
using the processor to transmit the at least one recommendation to the display unit.

2. The method of claim 1, further comprising:
using the processor to model the intervention or a part thereof on the anatomical model; and
using the processor to transmit a representation of the modeled intervention or part thereof to the display unit.

3. The method of claim 2, wherein the intervention includes one or more of: an insertion of an endoscopic device, a laparoscopic device, a stent, a prosthetic implant, a graft, or a needle; a bypass grafting procedure; a rotablation; an atherectomy; an angioplasty; an endarterectomy; a percutaneous coronary intervention; a carotid intervention; a peripheral intervention; a renal revascularization; a mesenteric revascularization; or an arteriovenous access procedure.

4. The method of claim 1, wherein the medical procedure is an invasive procedure.

5. The method of claim 1, wherein the medical procedure is a diagnostic procedure.

6. The method of claim 1, wherein the at least one associated characteristic is a blood flow characteristic, a location of one or more lesions or blockages, or a location of one or more interventional devices.

7. The method of claim 1, wherein the patient-specific data includes at least one of: data from an angiogram; data from optical coherence tomography; data from an intravenous ultrasound; blood pressure data; coronary flow data; cardiac contractility data; a measurement of a plaque; a local heart viability; data showing whether an occlusion is total or subtotal; data relating to the patient's physiological state; data relating to myocardial wall motions; stent position data; or data from a percutaneous coronary intervention.

8. The method of claim 1, wherein using the processor to determine a correspondence between the patient-specific data and at least one of the three-dimensional anatomical model or the at least one associated characteristic comprises using the processor to determine a location of the anatomical model to which the patient-specific data may apply.

9. The method of claim 1, wherein the display unit is located in a medical facility.

10. A computer-implemented method for automatically updating an anatomical model, the method comprising:
using a processor to determine a correspondence between patient-specific data from an interventional procedure and at least one of a patient-specific three-dimensional anatomical model of at least one cardiovascular vessel or at least one characteristic associated with the three-dimensional anatomical model;
using the processor to locate a discrepancy between the patient-specific data and at least one of the anatomical model or the at least one associated characteristic;
updating, using the processor, at least one of the anatomical model or the at least one associated characteristic to reduce the discrepancy;
transmitting, using the processor, an updated representation of at least one of the anatomical model or the at least one associated characteristic to a display device;
using the processor to generate at least one recommendation of an intervention on the patient based on at least one of the three-dimensional anatomical model or the at least one associated characteristic; and
using the processor to transmit the at least one recommendation to the display unit.

11. The method of claim 10, wherein the at least one associated characteristic is a blood flow characteristic.

12. The method of claim 10, further comprising:
using the processor to model the intervention on the anatomical model; and
using the processor to transmit a representation of the modeled intervention to the display unit.

13. The method of claim 10, further comprising:
periodically receiving, at the processor, refreshed patient-specific data from the interventional procedure;
using the processor to monitor for a new discrepancy between the refreshed patient-specific data and at least one of the anatomical model or the at least one associated characteristic; and
if a new discrepancy is found:
updating, using the processor, at least one of the anatomical model or the at least one associated characteristic to reduce the new discrepancy; and
transmitting, using the processor, an updated representation of at least one of the anatomical model or the at least one associated characteristic to the display device.

14. An anatomical modeling system comprising a processor, wherein the processor is configured to:
determine a correspondence between patient-specific data from a medical procedure and at least one of a patient-specific three-dimensional anatomical model of at least one cardiovascular vessel or at least one characteristic associated with the three-dimensional anatomical model;
identify a discrepancy between the patient-specific data and at least one of the three-dimensional anatomical model or the at least one associated characteristic;
modify at least one of the three-dimensional anatomical model or the at least one associated characteristic to reduce the discrepancy;
transmit an updated representation of at least one of the three-dimensional anatomical model or the at least one associated characteristic to the display unit;
generate at least one recommendation of an intervention on the patient based on at least one of the three-dimensional anatomical model or the at least one associated characteristic; and
transmit the at least one recommendation to the display unit.

15. The system of claim 14, wherein the processor is further configured to:
periodically receive refreshed patient-specific data from the interventional procedure;
monitor for a new discrepancy between the refreshed patient-specific data and at least one of the three-dimensional anatomical model or the at least one associated characteristic; and
if a new discrepancy is found:
update at least one of the three-dimensional anatomical model or the at least one associated characteristic to reduce the new discrepancy; and
transmit an updated representation of at least one of the three-dimensional anatomical model or the at least one associated characteristic to the display device.

16. The system of claim 14, wherein the at least one associated characteristic is a blood flow characteristic.

17. The system of claim 15, wherein the processor is further configured to:
  generate a model of the intervention on the anatomical model; and
  transmit a representation of the modeled intervention to the display unit.

* * * * *